United States Patent
Jabbour et al.

(10) Patent No.: US 7,615,210 B2
(45) Date of Patent: Nov. 10, 2009

(54) TREATMENT OF ENDOMETRIOSIS

(75) Inventors: Henry Nicolas Jabbour, Edinburgh (GB); Robert Peter Millar, Edinburgh (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 10/569,920

(22) PCT Filed: Aug. 24, 2004

(86) PCT No.: PCT/GB2004/003600

§ 371 (c)(1),
(2), (4) Date: Aug. 31, 2006

(87) PCT Pub. No.: WO2005/021750

PCT Pub. Date: Mar. 10, 2005

(65) Prior Publication Data

US 2006/0287258 A1    Dec. 21, 2006

(30) Foreign Application Priority Data

Aug. 29, 2003    (GB) .................................. 0320238.9

(51) Int. Cl.
*A61K 38/09* (2006.01)
*A61K 39/395* (2006.01)
*A61K 48/00* (2006.01)

(52) U.S. Cl. .............. 424/130.1; 424/134.1; 424/143.1; 514/15

(58) Field of Classification Search ........................ None
See application file for complete search history.

(56) References Cited

U.S. PATENT DOCUMENTS

| | | | |
|---|---|---|---|
| 6,121,230 A * | 9/2000 | Charnock-Jones et al. | 514/2 |
| 7,005,418 B1 * | 2/2006 | Riethmuller-Winzen et al. | 514/12 |
| 2002/0192634 A1 | 12/2002 | Ferrara et al. | |
| 2003/0059856 A1 | 3/2003 | Ames, Jr. et al. | |
| 2003/0099971 A1 | 5/2003 | Ni et al. | |
| 2003/0113867 A1 | 6/2003 | Zhou et al. | |

FOREIGN PATENT DOCUMENTS

| | | | |
|---|---|---|---|
| AU | 2003/204933 | | 1/2004 |
| EP | 1386615 A | | 2/2004 |
| JP | 2004-043468 | * | 2/2004 |
| WO | WO 94/10202 | * | 11/1994 |
| WO | WO 02/00711 A2 | | 1/2002 |
| WO | WO 03/020892 A2 | | 3/2003 |

OTHER PUBLICATIONS

Pelvic Mass in the Merck Manual.*
Endometriosis in the Merck Manual.*
Pelvic Mass in the Merck Manual, pp. 1-2. Accessed Apr. 19, 2007.*
Endometriosis in the Merck Manual, pp. 1-4. Accessed Mar. 13, 2007.*
Bartel & Szostak, "Isolation of New Ribozymes from a Large Pool of Random Sequences," *Science* 261:1411-1418 (1993).
Coombes et al., "Idoxifene: Report of a Phase I Study in Patients with Metastatic Breast Cancer," *Cancer Res.* 55:1070-1074 (1995).
Derossi et al., "Trojan Peptides: The Penetratin System for Intracellular Delivery," *Trends Cell Biol.* 8:84-87 (1998).
Genbank Accession No. AAM48127 (Jun. 6, 2002).
Genbank Accession No. AAM48128 (Jun. 6, 2002).
Genbank Accession No. AF506287 (Jun. 6, 2002).
Genbank Accession No. AF506288 (Jun. 6, 2002).
Genbank Accession No. NM_032414 (Apr. 6, 2003).
Genbank Accession No. NP_068754 (Apr. 6, 2003).
Genbank Accession No. NP_115790 (Apr. 6, 2003).
Genbank Accession No. Q9HC23 (Sep. 15, 2003).
Harper-Wynne & Coombes, "Anastrozole Shows Evidence of Activity in Postmenopausal Patient Who Have Responded or Stabilised on Formestane Therapy," *Eur. J. Cancer* 35:744-746 (1999).
Labrie et al., "EM-652 (SCH57068), a Pure SERM Having Complete Antiestrogenic Activity in the Mammary Gland and Endometrium," *J. Steroid Biochem. Mol. Biol.* 79:213-225 (2001).
LeCouter et al., "Identification of an Angiogenic Mitogen Selective for Endocrine Gland Endothelium" *Nature* 412:877-884 (2001).
LeCouter et al., "The Endocrine-Gland-Derived VEGF Homologue Bv8 Promotes Angiogenesis in the Testis: Localization of Bv8 Receptors to Endothelial Cells," *Proc. Natl. Acad. Sci. USA* 100:2685-2690 (2003).
Li et al., "Identification of Two Prokineticin cDNAs: Recombinant Proteins Potently Contract Gastrointestinal Smooth Muscle," *Mol. Pharmacol.* 59(4):692-698 (2001).
Lin et al., "Identification and Molecular Characterization of Two Closely Related G Protein-Coupled Receptors Activated by Prokineticins/Endocrine Gland Vascular Endothelial Growth Factor," *J. Biol. Chem.* 277(22):19276-19280 (2002).
Lin et al., "Characterization of Endocrine Gland-Derived Vascular Endothelial Growth Factor Signaling in Adrenal Cortex Capillary Endothelial Cells," *Biol. Chem.* 277(10):8724-8729 (2002).
Masuda et al., "Isolation and Identification of EG-VEGF/Prokineticins as Cognate Ligands for Two Orphan G-Protein-Coupled Receptors," *Biochem. Biophys. Res. Comm.* 293:396-402 (2002).
Noyes et al., "Dating the Endometrial Biopsy," *Am. J. Obstet. Gynecol.* 122(2):262-263 (1975).
Smith, "Regulation of Angiogenesis in the Endometrium," *TRENDS Endocrinol. Metab.* 12(4):147-151 (2001).
Soga et al., "Molecular Cloning and Characterization of Prokineticin Receptors," *Biochim. et Biophys. Acta* 1579:173-179 (2002).

* cited by examiner

*Primary Examiner*—Cecilia Tsang
*Assistant Examiner*—Julia Ha
(74) *Attorney, Agent, or Firm*—Nixon Peabody LLP

(57) ABSTRACT

A method of combating menorrhagia, dysmenorrhoea or endometriosis in a female individual that includes administering to the individual at least one agent that reduces the effect of prokineticin 1 on a prokineticin receptor.

5 Claims, 4 Drawing Sheets

TREATMENT OF ENDOMETRIOSIS

CROSS-REFERENCE TO RELATED APPLICATIONS

This application is a national stage application under 35 U.S.C. § 371 from PCT Application No. PCT/GB2004/003600, filed Aug. 24, 2004, which claims the priority benefit of Great Britain Application No. 0320238.9, filed Aug. 29, 2003.

FIELD OF THE INVENTION

The present invention relates to methods of treatment, and in particular methods of treating menorrhagia, dysmenorrhoea and endometriosis.

BACKGROUND OF THE INVENTION

Menorrhagia is over-abundance of the menstrual discharge. Dysmenorrhoea means painful menstruation. Endometriosis is the ectopic implantation and growth of endometrium and can therefore be considered as abnormal growth of cells of the endometrium.

Menorrhagia, dysmenorrhoea and endometriosis affect many women, particularly in the Western world, and represent a significant health problem. At least one in 20 women in the UK aged between 34 and 49 years will consult their general practitioners because of menstrual problems. These women account for more than one in ten of all gynaecological referrals and cost the NHS in excess of £7 million per year for medical prescriptions alone. Perceived abnormal vaginal bleeding is said to account for 70% of the at least 70,000 hysterectomies done each year.

At present, the treatments used for menorrhagia include tranexamic acid or mefenamic acid. In severe cases the treatment is hysterectomy (vaginal or abdominal) but this is a major operation with serious morbidity and some risk of death. A review of treatments for menorrhagia is Stirrat (1999) *The Lancet* 353, 2175-2176. The development of further and alternative therapies is desirable.

Angiogenesis is of crucial importance in cyclical tissue regeneration and growth in the endometrium and in the development of endometrial disorders including menorrhagia and endometriosis. A major role in the control of endometrial angiogenesis has been established for a number of factors including the VEGF family of genes and their receptors and the fibroblast growth factors (Smith (2001) *Trends Endocrinol. Metab.* 12[4]: 147-51). However, the mechanisms of angiogenesis in the endometrium remain to be fully elucidated.

The prokineticins, prokineticin 1 (PK1), also known as endocrine-gland-derived vascular endothelial growth factor (EG-VEGF) and prokineticin 2 (PK2), also known as Bv8, are two-recently identified angiogenic factors having 60% sequence identity (LeCouter et al (2001) *Nature* 412: 877-884; Li et al (2001) *Mol. Pharmacol.* 59: 692-698; and LeCouter et al (2003) *Proc. Natl. Acad. Sci. USA* 100: 2685-2690). PK1 mRNA expression has been described in a variety of tissues including steroidogenic glands, namely, ovary, testis and adrenal gland and other tissues including the gastrointestinal tract, nervous system, bladder and prostate (LeCouter et al (2001); Li et al (2001)). PK2 expression shows a similar distribution, but is generally weaker with strongest expression in the testis and peripheral blood leukocytes (Li et al (2001); LeCouter et al (2003)). Analysis by RNA or Northern hybridisation has demonstrated low levels of PK1 and PK2 expression in the human uterus, but with greater expression of PK1 (Li et al (2001)).

The prokineticins are ligands for two closely homologous G protein-coupled receptors, prokineticin receptor 1 (PKR1) and prokineticin receptor 2 (PKR2), activation of which leads to calcium mobilisation, stimulation of phosphoinositide turnover and activation of the MAP kinase signalling pathway. Expression of the prokineticin receptors has been identified in a number of tissues including testis, skin, and the central nervous system (Lin et al (2002) *J. Biol. Chem.* 277 [22]: 19276-280; Soga et al (2002) *Biochimica et Biophysica Acta* 1579: 173-179).

Initial studies examining the functions of PK1 and PK2 have demonstrated that they promote angiogenesis by causing endothelial cell proliferation and chemotaxis in an organ specific manner (LeCouter et al (2001); LeCouter et al (2003)). In addition, there is evidence that they are secreted in response to hypoxia and are involved in the transmission of the circadian rhythm of the suprachiasmatic nucleus (LeCouter et al (2001); Cheng et al (2002) *Nature* 417: 405-410).

WO 02/00711 (Genentech, Inc.) describes PK1 (referred to as EG-VEGF) and speculates upon its biological role. WO 02/00711 states that EG-VEGF or agonist or antagonists thereof may be useful in treating a number of disease conditions including cancers such as uterine cancer and endometrial carcinoma. It does not disclose or suggest using an antagonist of EG-VEGF to treat other uterine conditions such as menorrhagia, dysmenorrhoea or endometriosis.

SUMMARY OF THE INVENTION

We have examined expression of the prokineticins and the prokineticin receptors in the uterus across the menstrual cycle, and demonstrated higher levels of PK1 expression during the secretory phase of the endometrium compared with other stages. PK1 expression is also elevated in the menstrual phase as well. Both of the prolineticin receptors PKR1 and PKR2 have increased expression in the menstrual phase of the cycle compared with other stages of the cycle. We have also localised PK1 by immunohistochemistry to glandular epithelial, stromal and vascular endothelial cells in the endometrium and endothelial and smooth muscle cells in the myometrium. These observations demonstrate the possibility of reducing or preventing the effect of PK1 on a prokineticin receptor, to combat menorrhagia, dysmenorrhoea and endometriosis.

in the functional (F) (FIG. 2e) and basal (B) (FIG. 2f) layers with stronger reactivity towards the surface epithelium (SE). Reactivity was detected in stromal cells and endothelial cells (see arrows in FIG. 2f) predominantly in the functional layer.

Figure 3:
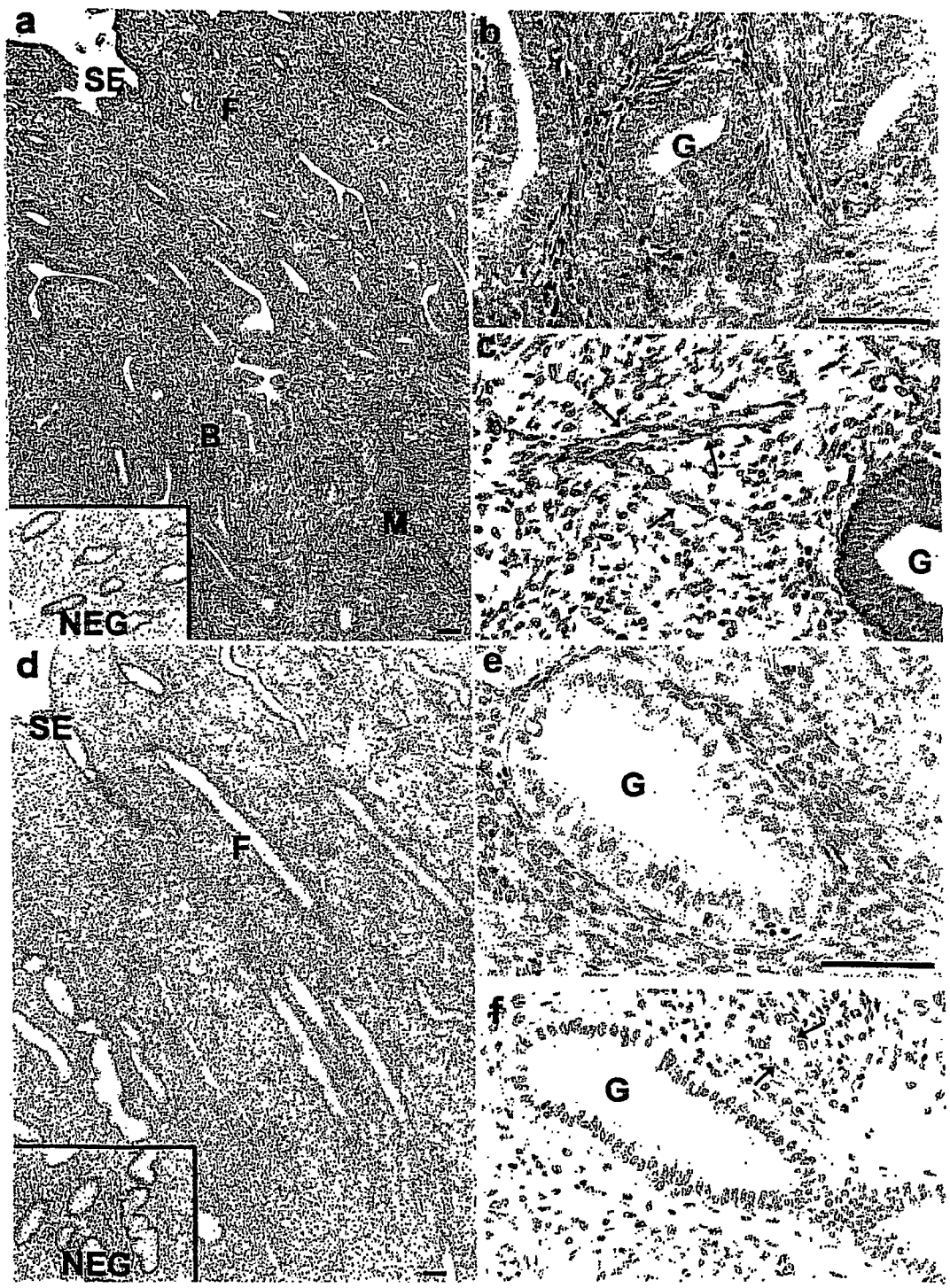

FIGS. 3a-3c: In situ hybridisation of PKR1 in human endometrial tissue (functional layer and basal-myometrial junction). Strong staining was detected in the functional layer (F) in glandular epithelial cells (G) and stromal cells (FIG. 3b) and glandular epithelial cells in the basal layer (B). PKR1 was also expressed in endothelial cells (see arrows in FIG. 3c) throughout the endometrium and myometrium (M) and in myometrial smooth muscle cells. NEG=Negative control; Scale bars=100 µM (FIG. 3a) and 50 µM (FIG. 3b), SE=surface epithelium.

FIGS. 3d-3f: In situ hybridisation of PKR2 in human endometrial tissue (functional layer and basal-myometrial junction). Weak expression of PKR2 was detected predominantly in the functional layer of the endometrium (F) in glandular epithelial cells (G) and endothelial cells (see arrows in FIG. 3f). NEG=Negative control; Scale bars=100 µM (FIG. 3d) and 50 µM (FIG. 3e), SE=surface epithelium.

Figure 4:
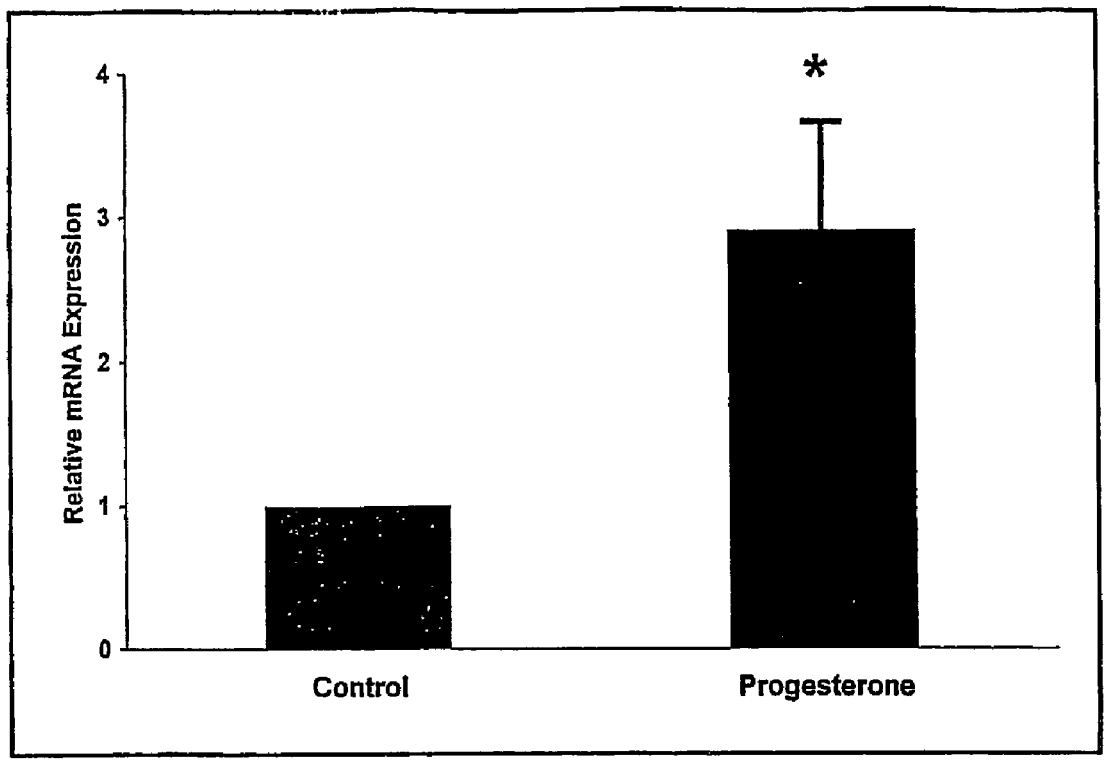

FIG. 4: PK1 expression in endometrial tissue (n=5) in response to treatment with 1 µM progesterone for 24 hours. Results are expressed as mean fold increase in PK1+SEM (* denotes $p<0.05$).

DETAILED DESCRIPTION OF THE INVENTION

A first aspect of the invention provides a method of combating menorrhagia, dysmenorrhoea or endometriosis in a female individual, the method comprising administering to the individual at least one agent that reduces the effect of prokineticin 1 (PK1) on a prokineticin receptor (PKR).

The method may be used to alleviate symptoms of menorrhagia, dysmenorrhoea or endometriosis (ie palliative use), or may be used to reduce the severity of the condition(s), or may be used to treat the condition(s), or may be used prophylactically to prevent the condition(s). Thus by "combating" a disease or condition we include the meaning of treating, reducing or preventing the disease or condition, or alleviating the symptoms of the disease or condition.

The invention thus includes a method of treating, reducing or preventing menorrhagia, dysmenorrhoea or endometriosis in a female individual, or alleviating the symptoms of menorrhagia, dysmenorrhoea or endometriosis in a female individual, the method comprising administering to the individual at least one agent that reduces the effect of PK1 on a PKR.

A second aspect of the invention provides the use of at least one agent that reduces the effect of PK1 on a PKR in the preparation of a medicament for combating menorrhagia, dysmenorrhoea or endometriosis in a female individual.

The invention thus includes the use of at least one agent that reduces the effect of PK1 on a PKR in the preparation of a medicament for treating, reducing or preventing menorrhagia, dysmenorrhoea or endometriosis in a female individual, or for alleviating the symptoms of menorrhagia, dysmenorrhoea or endometriosis in a female individual.

By PK1 we include the gene product of the human prokineticin 1 gene (PROK1) and naturally occurring variants thereof. The cDNA and amino acid sequence of human PK1 are found in Genbank Accession Nos. NM_032414 and NP_115790. PK1 is also described by LeCouter et al (2001) and in WO 02/00711.

PK1 has been shown to be a ligand for both PKR1 and PKR2 (Masuda et al (2002) *Biochemical and Biophysical Research Communications* 293: 396-402; Soga et al (2002); Lin et al (2002)). Thus by an agent that reduces the effect of PK1 on a PKR, we include an agent that reduces the effect of PK1 on PKR1 and an agent that reduces the effect of PK1 on PKR2.

By PKR1 we include the gene product of the human prokineticin receptor 1 gene (PKR1) and naturally occurring variants thereof. The cDNA and amino acid sequence of human PKR1 are found in Genbank Accession Nos. AF506287 and AAM48127.

By PKR2 we include the gene product of the human prokineticin receptor 2 gene (PKR2) and naturally occurring variants thereof. The cDNA and amino acid sequence of human PKR2 are found in Genbank Accession Nos. AF506288 and AAM48128.

It is possible to have menorrhagia, dysmenorrhoea and/or endometriosis together and the methods and uses of the present invention may be used to combat these conditions in the same patient. Alternatively, the methods and uses can be used to combat either menorrhagia, dysmenorrhoea and endometriosis separately.

Thus the invention includes a method of combating menorrhagia in a female individual, the method comprising administering to the individual at least one agent that reduces the effect of PK1 on a PKR.

The invention includes the use of at least one agent that reduces the effect of PK1 on a PKR in the preparation of a medicament for combating menorrhagia in a female individual.

The invention also includes a method of combating dysmenorrhoea in a female individual, the method comprising administering to the individual at least one agent that reduces the effect of PK1 on a PKR.

The invention thus includes the use of at least one agent that reduces the effect of PK1 on a PKR in the preparation of a medicament for combating dysmenorrhoea in a female individual.

The invention also includes a method of combating endometriosis in a female individual, the method comprising administering to the individual at least one agent that reduces the effect of PK1 on a PKR.

The invention thus includes the use of at least one agent that reduces the effect of PK1 on a PKR in the preparation of a medicament for combating endometriosis in a female individual.

The female individual may be any individual who is suffering from menorrhagia, dysmenorrhoea and/or endometriosis or who is at risk from these conditions.

Any premenopausal or perimenopausal woman is at risk of menorrhagia and/or dysmenorrhoea; however, menorrhagia is more common at the beginning and end of a woman's reproductive life so typically there is a greater risk when a woman's periods first start and in women over 40 years of age.

The patient to be treated may be any female individual who would benefit from such treatment. Typically and preferably the patient to be treated is a human female. However, the methods of the invention may be used to treat female mammals, such as the females of the following species: cows, horses, pigs, sheep, cats and dogs. Thus, the methods have uses in both human and veterinary medicine.

It is appreciated that for non-human aspects of the invention, such as methods of veterinary treatment, an agent that reduces the effect of PK1 on a PKR is preferably one that has this effect in the species to be treated.

Typically, the agent that reduces the effect of PK1 on a PKR is one which prevents, reduces or disrupts PK1-mediated signalling of a PKR.

In an embodiment of the present invention, it is preferred if the agent that reduces the effect of PK1 on a PKR does not prevent PK2 having its effect on a PKR (whether fully or partially). In this embodiment, it is preferred if the agent that reduces the effect of PK1 on a PKR does not significantly reduce the effect of PK2 on a PKR, or does not reduce the effect of PK2 on a PKR at all (or only does so at an undetectable level). Thus, preferably, the agent that reduces the effect of PK1 on a PKR targets PK1 itself, or an interaction between PK1 and a PKR.

Preferably, an agent that reduces the effect of PK1 on a PKR prevents, reduces or disrupts the binding of PK1 to a PKR. Alternatively or additionally, the agent may affect the interaction between PK1 and a PKR, or the interaction between a PKR and the associated G protein, thus inhibiting or disrupting the PK1-PKR mediated signal transduction pathway.

In a preferred embodiment, the agent may be an antagonist of PK1. PK1 antagonists are typically molecules which bind to PK1 and prevent, reduce or disrupt PK1 binding to its receptor, which inhibits or disrupts the PK1-PKR mediated signal transduction pathway. This is the 'soluble receptor' approach in which typically either a part of the receptor or an antibody binds to PK1.

The term "antagonist" is used in the broadest sense, and includes any molecule that partially or fully blocks, prevents, inhibits, reduces or neutralises a biological activity of PK1. Suitable antagonist molecules specifically include antibodies or antibody fragments, fragments or amino acid sequence variants of PK1 or of a PKR, peptides and small organic molecules, In another preferred embodiment, the agent that reduces the effect of PK1 on a PKR may be an agent that prevents, reduces or disrupts the expression of PK1 or a PKR. The agent may prevent, reduce or disrupt transcription of the PROK1, PKR1 or PKR2 genes, or may prevent, reduce or disrupt stability or translation of the gene transcripts. Suitable agents may include small interfering RNA molecules, antisense oligonucleotides, triplex-forming oligonucleotides and ribozymes.

Alternatively, the PK1 antagonist may be a molecule which binds to PK1 without preventing or reducing the binding of PK1 to a PKR, but which disrupts the interaction between PK1 and a PKR such that the PK1-PKR mediated signal transduction pathway is inhibited or disrupted. This could be a molecule which binds in a covalent fashion to PK1 and has no effect on binding potency but affects the signal transduction mechanisms.

In one preferred embodiment, the agent that reduces the effect of PK1 on a PKR comprises an antagonist of a PKR, which may be any PKR antagonist that is suitable to be administered to a patient. The receptor antagonists are typically selective to the particular receptor and preferably have an equal or higher binding affinity to a PKR than does PK1 itself. Although antagonists with a higher affinity for the receptor than the natural ligand are preferred, antagonists with a lower affinity may also be used, but it may be necessary to use these at higher concentrations. Preferably, the antagonists bind reversibly to a PKR. Preferably, antagonists are selective for a particular receptor and do not affect other receptors; thus, typically, a PKR antagonist binds one PKR but does not substantially bind any other PKR.

In an embodiment, the agent that reduces the effect of PK1 on a PKR may be an antagonist of a PKR. PKR antagonists are typically molecules which bind to a PKR, compete with the binding of the natural ligand PK1, and inhibit or disrupt the PK1-PKR mediated signal transduction pathway.

In an embodiment, reducing the effect of PK1 on a PKR includes occupying the PK1 binding site on the PKR, such that the natural ligand (PK1) is inhibited (whether fully or partially) from binding in a mode that would result in its normal mode of signalling via Gαq.

Alternatively, the receptor antagonist may be a molecule which binds to a PKR without preventing PK1 binding thereto, but which disrupts the normal interaction between PK1 and a PKR, thus inhibiting, reducing or disrupting PK1-PKR mediated signal transduction pathway.

Further alternatively, a PKR antagonist may be a molecule which binds to a PKR and which disrupts the interaction between a PKR and the associated G protein, thus inhibiting or disrupting the PK1 mediated signal transduction pathway.

More specific examples of potential antagonists include anti-PK1 antibodies and anti-PKR antibodies. By antibodies we include, without limitation, poly- and monoclonal antibodies and antibody fragments, single-chain antibodies, anti-idiotypic antibodies, and chimeric or humanised versions of such antibodies or fragments, as well as human antibodies and antibody fragments.

The anti-PK1 or anti-PKR antibodies may comprise polyclonal antibodies. Methods of preparing polyclonal antibodies are known to the skilled artisan. Polyclonal antibodies can be raised in a mammal, for example, by one or more injections of an immunising agent and, if desired, an adjuvant. Typically, the immunising agent and/or adjuvant will be injected in the mammal by multiple subcutaneous or intraperitoneal injections. The immunising agent may include the PK1 polypeptide or a fusion protein thereof. It may be useful to conjugate the immunising agent to a protein known to be immunogenic in the mammal being immunised. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunisation protocol may be selected by one skilled in the art without undue experimentation.

Alternatively, and more preferably, the antibodies may be monoclonal antibodies. Monoclonal antibodies may be prepared using hybridoma methods, such as those described by Kohler and Milstein, *Nature*, 256: 495 (1975). In a hybridoma method, a mouse, hamster, or other appropriate host animal, is typically immunised with an immunising agent to elicit lymphocytes that produce or are capable of producing antibodies that will specifically bind to the immunising agent. Alternatively, the lymphocytes may be immunised in vitro.

The immunising agent will typically include the PK1 polypeptide or PKR polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalised cell line using a suitable fusing agent, such as polyethylene glycol, to form a hybridoma cell (Goding, *Monoclonal Antibodies: Principles and Practice*, Academic Press, (1986) pp. 59-103). Immortalised cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalised cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalised cell lines are those that fuse efficiently, support stable high level expression of antibody by the selected antibody-producing cells, and are sensitive to a medium such as HAT medium. More preferred immortalised cell lines are murine myeloma lines, which can be obtained, for instance, from the Salk Institute Cell Distribution Center, San Diego, Calif. and the American Type Culture Collection (ATCC). Human myeloma and mouse-human heteromyeloma cell lines also have been described for the production of human monoclonal antibodies (Kozbor, *J. Immunol.*, 133: 3001 (1984); Brodeur et al, *Monoclonal Antibody Production Techniques and Applications*, Marcel Dekker, Inc., New York, (1987) pp. 51-63).

The culture medium in which the hybridoma cells are cultured can then be assayed for the presence of monoclonal antibodies. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107: 220 (1980).

After the desired hybridoma cells are identified, the clones may be subcloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

In a preferred embodiment, the antibodies may be humanised antibodies or human antibodies. Humanised forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanised antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanised antibodies may also comprise residues which are found neither in the recipient antibody nor in the imported CDR or framework sequences. In general, the humanised antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanised antibody optimally also will comprise at least a portion of an immunoglobulin constant region (Fc), typically that of a human immunoglobulin (Jones et al, *Nature,* 321: 522-525 (1986); Riechmann et al, *Nature,* 332: 323-329 (1988); and Presta, *Curr. Op. Struct. Biol.,* 2: 593-596 (1992)).

Methods for humanising non-human antibodies are well known in the art. Generally, a humanised antibody has one or more amino acid residues introduced into it from a source which is non-human. These non-human amino acid residues are often referred to as "import" residues, which are typically taken from an "import" variable domain. Humanisation can be essentially performed following the method of Winter and co-workers (Jones et al, (1986); Riechmann et al, (1988); Verhoeyen et al, *Science,* 239: 1534-1536 (1988)), by substituting rodent CDRs or CDR sequences for the corresponding sequences of a human antibody. Accordingly, such "humanised" antibodies are chimeric antibodies (U.S. Pat. No. 4,816,567), wherein substantially less than an intact human variable domain has been substituted by the corresponding sequence from a non-human species. In practice, humanised antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.,* 227: 381 (1991); Marks et al., *J. Mol. Biol.,* 222: 581 (1991)). The techniques of Cole et al. and Boerner et al. are also available for the preparation of human monoclonal antibodies (Cole et al, *Monoclonal Antibodies and Cancer Therapy*, Alan R. Liss, p. 77 (1985) and Boerner et al, *J. Immunol.,* 147[1]: 86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, *Bio/Technology* 10: 779-783 (1992); Lonberg et al, *Nature* 368: 856-859 (1994); Morrison, *Nature* 368: 812-13 (1994); Fishwild et al, *Nature Biotechnology* 14: 845-51 (1996); Neuberger, *Nature Biotechnology* 14: 826 (1996); Lonberg and Huszar, *Intern. Rev. Immunol.* 13: 65-93 (1995).

Bispecific antibodies are monoclonal, preferably human or humanised, antibodies that have binding specificities for at least two different antigens. In the present case, one of the binding specificities is for the PK1 or PKR, the other one is for any other antigen, and preferably for a cell-surface protein or receptor or receptor subunit. Alternatively, bispecific antibodies may bind to two different epitopes on PK1 or a PKR.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein & Cuello, *Nature*, 305: 537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., *EMBO J.*, 10: 3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al, *Methods in Enzymology*, 121: 210 (1986).

According to another approach described in WO 96/27011, the interface between a pair of antibody molecules can be engineered to maximise the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. Fab bispecific antibodies). Techniques for generating bispecific antibodies from antibody fragments have been described in the literature. For example, bispecific antibodies can be prepared can be prepared using chemical linkage. Brennan et al, *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilise vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilisation of enzymes.

Fab' fragments may be directly recovered from *E. coli* and chemically coupled to form bispecific antibodies. Shalaby et al, *J. Exp. Med.* 175: 217-225 (1992) describe the production of a fully humanised bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al, *J. Immunol.* 148[5]: 1547-1553 (1992). The leucine zipper peptides from the Fos and Jun proteins were linked to the Fab' portions of two different antibodies by gene fusion. The antibody homodimers were reduced at the hinge region to form monomers and then re-oxidised to form the antibody heterodimers. This method can also be utilised for the production of antibody homodimers. The "diabody" technology described by Hollinger et al, *Proc. Natl. Acad. Sci. USA* 90: 6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al, *J. Immunol.* 152: 5368 (1994). Antibodies with more than two valencies are contemplated. For example, trispecific antibodies can be prepared. Tutt et al, *J. Immunol.* 147: 60 (1991).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The antibodies may also be formulated as immunoliposomes. Liposomes containing the antibody are prepared by methods known in the art, such as described in Epstein et al, *Proc. Natl. Acad. Sci. USA*, 82: 3688 (1985); Hwang et al, *Proc. Natl. Acad. Sci. USA*, 77: 4030 (1980); and U.S. Pat.

Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatised phosphatidyl-ethanolamine (PEG-PE). Liposomes are extruded through filters of defined pore size to yield liposomes with the desired diameter. Fab' fragments of the antibody of the present invention can be conjugated to the liposomes as described in Martin et al, *J. Biol. Chem,* 257: 286-288 (1982) via a disulfide-interchange reaction. Liposomes can also be used to deliver the antibody, or an antibody fragment, into cells.

Where antibody fragments are administered to a patient, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesised chemically and/or produced by recombinant DNA technology. See, for example, Marasco et al, *Proc. Natl. Acad. Sci. USA,* 90: 7889-7893 (1993).

Anti-PK1 antibodies that may be suitable for use in the present invention include the anti-PK1 monoclonal antibodies 1C6, 2A3, 2A8 and 4H9 described in Published US Patent Application No. 2002/0192634 A1 to Ferrara et al (Genentech, Inc.) and which were reported to neutralise PK1 (EG-VEGF) activity. Antibody 4H9 was reported to completely neutralise the activity of 10 nM EG-VEGF when added at a dose of 10 μg/ml or higher (Example 21). The entire disclosure of US 2002/0192634 relating to anti-PK1 antagonists, and in particular anti-PK1 antibodies, is incorporated herein by reference. Material No. DNA60621-1516 was deposited at the American Type Culture Collection (ATCC) on 4 Aug. 1998 under Deposit No. 203091.

Another potential agent that reduces the effect of PK1 on a PKR is an antisense nucleic acid molecule, where, for example, an antisense RNA or DNA molecule acts to block directly the translation of mRNA by hybridising to targeted mRNA and preventing protein translation. Suitable antisense oligonucleotides, which can be RNA or DNA, having specificity for PK1 or a PKR can be designed based upon their known nucleotide sequences (see above), and this is well within the skill and abilities of a person of average skill in the art.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene.

Antisense technology can be used to control gene expression through triple-helix formation (see below) or antisense DNA or RNA, both of which methods are based on binding of a polynucleotide to DNA or RNA. For example, the 5' coding portion of the polynucleotide sequence, which encodes the mature PK1 polypeptides herein, is used to design an antisense RNA oligonucleotide of from about 10 to 40 base pairs in length. The antisense oligonucleotide hybridises to the mRNA in vivo and blocks translation of the mRNA molecule into a polypeptide (Okano, *Neurochem.,* 56: 560 (1991); *Oligodeoxynucleotides as Antisense Inhibitors of Gene Expression* (CRC Press: Boca Raton, Fla., USA, 1988). The oligonucleotides described above can also be delivered to cells such that the antisense RNA may be expressed in vivo to inhibit production of the polypeptide. When antisense DNA is used, oligodeoxyribonucleotides derived from the translation-initiation site, e.g., between about −10 and +10 positions of the target gene nucleotide sequence, are preferred.

By binding to the target nucleic acid, the above oligonucleotides can inhibit the function of the target nucleic acid. This could, for example, be a result of blocking the transcription, processing, poly(A) addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. (1988) *Proc. Natl. Acad. Sci. (USA)* 85[15]: 5507-11). The Goodchild study showed that oligonucleotides that were most effective were complementary to the poly(A) signal; also effective were those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Typically, antisense oligonucleotides are 15 to 35 bases in length. For example, 20-mer oligonucleotides have been shown to inhibit the expression of the epidermal growth factor receptor mRNA (Witters et al, *Breast Cancer Res Treat* 53:41-50 (1999)) and 25-mer oligonucleotides have been shown to decrease the expression of adrenocorticotropic hormone by greater than 90% (Frankel et al, *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079-7083 showed increased inhibition in tissue culture of HIV-1 using oligonucleotide phosphoramidates and phosphorothioates. Sarin et al (1988) *Proc. Natl. Acad. Sci. USA* 85, 7448-7451 demonstrated increased inhibition of HIV-1 using oligonucleotide methylphosphonates. Agrawal et al (1989) *Proc. Natl. Acad. Sci. USA* 86, 7790-7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430-3434 report inhibition in tissue culture of influenza virus replication by oligonucleotide phosphorothioates.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*.

The synthesis of oligonucleotides having one or more of these linkages substituted for the phosphodiester internucleotide linkages is well known in the art, including synthetic pathways for producing oligonucleotides having mixed internucleotide linkages. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) *Tetrahedron Letters* 28, 3401; Bannwarth (1988) *Helv. Chim. Acta.* 71, 1517; Crosstick and Vyle (1989) *Tetrahedron Letters* 30, 4693; Agrawal et al (1990) *Proc. Natl. Acad. Sci. USA* 87, 1401-1405, the teachings of which are incorporated herein by reference. Other methods for synthesis or production also are possible.

Oligonucleotides can be made resistant to degradation by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747-750 and Agrawal et al (1991) *Proc. Natl. Acad. Sci. USA* 88[17], 7595-7599, the teachings of which are hereby incorporated herein by reference.

A further method of making oligonucleotides resistant to nuclease attack is for them to be "self-stabilized" as described by Tang et al (1993) *Nucl. Acids Res.* 21, 2729-2735 incorporated herein by reference. Self-stabilized oligonucleotides have hairpin loop structures at their 3' ends, and show increased resistance to degradation by snake venom phosphodiesterase, DNA polymerase I and fetal bovine serum. The self-stabilized region of the oligonucleotide does not interfere in hybridization with complementary nucleic acids, and pharmacokinetic and stability studies in mice have shown increased in vivo persistence of self-stabilized oligonucleotides with respect to their linear counterparts.

The agent that reduces the effect of PK1 on a PK receptor may be a an oligonucleotide that promotes triple-helix formation with the PK1 gene or a PKR gene.

Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites.

Nucleic acid molecules for triple-helix formation to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see WO 97/33551.

As with antisense methods, this is based on the binding of a polynucleotide sequence to DNA or RNA. Polynucleotides suitable for use in these methods are preferably 20 to 40 bases in length and are designed to be complementary to a region of the gene involved in transcription (Lee et al., Nucl. Acids Res. 6: 3073 (1979); Cooney et al, *Science* 15241: 456 (1988); and Dervan et al., *Science* 251: 1360 (1991)). Triple helix-formation optimally results in a shut-off of RNA transcription from DNA. Suitable oligonucleotides having specificity for PK1 can be designed based upon their known nucleotide sequences (see above), and is well within the skill and abilities of a person of average skill in the art.

The agent that reduces the effect of PK1 on a PK receptor may be a ribozyme. Ribozymes are enzymatic RNA molecules capable of catalysing the specific cleavage of RNA. Ribozymes act by sequence-specific hybridisation to the complementary target RNA, followed by endonucleolytic cleavage. Specific ribozyme cleavage sites within a potential RNA target can be identified by known techniques. For further details see, e.g., Rossi, *Current Biology*, 4: 469-471 (1994), and WO 97/33551. Thus, ribozymes (e.g., hammerhead ribozymes (described in Haselhoff & Gerlach (1988) *Nature* 334: 585-591)) can be used to catalytically cleave mRNA transcripts to thereby inhibit translation of an mRNA.

A ribozyme having specificity for PK1 or a PKR can be designed based upon their known nucleotide sequences (see above), and is well within the skill and abilities of a person of average skill in the art. Alternatively, PK1 mRNA can be used to select a catalytic RNA having a specific ribonuclease activity from a pool of RNA molecules. See, e.g., Bartel et al., (1993) *Science* 261: 1411-1418.

The agent that reduces the effect of PK1 on a PK receptor may be a small interfering RNA (siRNA) molecule. RNA interference (RNAi) is the process of sequence-specific post-transcriptional gene silencing in animals initiated by double-stranded (dsRNA) that is homologous in sequence to the silenced gene. The mediators of sequence-specific mRNA degradation are typically 21- and 22-nucleotide small interfering RNAs (siRNAs) which, in vivo, may be generated by ribonuclease III cleavage from longer dsRNAs. Elbashir et al. (2001*, Nature* 411, 494-498) has shown that 21-nucleotide siRNA duplexes specifically suppress expression of both endogenous and heterologous genes in, for example, mammalian cells. In mammalian cells it is believed that the siRNA has to be comprised of two complementary 21mers as described below since longer double-stranded (ds) RNAs will activate PKR (dsRNA-dependent protein kinase) and inhibit overall protein synthesis.

Duplex siRNA molecules selective for PK1 can readily be designed by reference to the PK1 cDNA sequence (see above). Typically, the first 21-mer sequence that begins with an AA dinucleotide which is at least 120 nucleotides downstream from the initiator methionine codon is selected. The RNA sequence perfectly complementary to this becomes the first RNA oligonucleotide. The second RNA sequence should be perfectly complementary to the first 19 residues of the first, with an additional UU dinucleotide at its 3' end. Once designed, the synthetic RNA molecules can be synthesised using methods well known in the art.

Other potential PK1 antagonists include small molecules that bind to the active site, the receptor binding site, or other relevant binding site of PK1, thereby blocking its normal biological activity. Examples of small molecules include, but are not limited to, small peptides or peptide-like molecules, preferably soluble peptides, and synthetic non-peptidyl organic or inorganic compounds.

Thus, in an embodiment, a PK1 antagonist may be a closely related protein, for example, a mutated form of the PK1 polypeptide, that recognises a PKR but imparts no effect, thereby competitively inhibiting the action of the PK1 polypeptide on the PKR.

A range of methods for identifying agents that reduce the effect of PK1 on a PKR (ie antagonists) that may be suitable for use in the present invention are described in detail in WO 02/00711 and in US patent application no. 2002/0192634, both of which are incorporated herein by reference.

In an embodiment, overexpression of an agonist can serve as an antagonist wherein activity is regulated by positive feedback.

Any agent that reduces the effect of PK1 on a PKR may be referred to as a treatment agent of the invention or as a compound of the invention.

The treatment agent(s) are administered to the female individual in an effective amount to combat the menorrhagia, dysmenorrhoea or endometriosis. The treatment agent may be administered by any suitable route, and in any suitable form.

In an embodiment, the treatment agent(s) for use in the invention is administered in a quantity and frequency such that an effective dose is delivered to at least 75% of the PKRs, ($ED_{75}$) and more preferably at least 90% of the PKRs ($ED_{90}$). The potency of the molecule(s) would dictate the dose, as would the formulation and route of administration.

The aforementioned treatment agents for use in the invention or a formulation thereof may be administered by any conventional method including oral and parenteral (eg subcutaneous or intramuscular) injection. The treatment may consist of a single dose or a plurality of doses over a period of time. The dose to be administered is determined upon consideration of age, body weight, mode of administration, duration of the treatment and pharmacokinetic and toxicological properties of the treatment agent or agents. The treatment agents are administered at a dose (or in multiple doses) which produces a beneficial therapeutic effect in the patient. Typically, the treatment agents are administered at a dose the same as or similar to that used when the treatment agent is used for another medical indication. In any event, the dose suitable for treatment of a patient may be determined by the physician.

Whilst it is possible for a treatment agent of the invention to be administered alone or in combination with other said treatment agents, it is preferable to present it or them as a pharmaceutical formulation, together with one or more acceptable carriers. The carrier(s) must be "acceptable" in the sense of being compatible with the treatment agent of the invention and not deleterious to the recipients thereof. Typically, the carriers will be water or saline which will be sterile and pyrogen free.

The formulations may conveniently be presented in unit dosage form and may be prepared by any of the methods well known in the art of pharmacy. Such methods include the step of bringing into association the treatment agent or agents with the carrier which constitutes one or more accessory ingredients. In general the formulations are prepared by uniformly and intimately bringing into association the active ingredient (ie treatment agent or agents) with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier. Buccal administration is also preferred.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

Certain of the treatment agents are proteins or peptides. Proteins and peptides may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The protein and peptide can be administered by a surgically implanted device that releases the drug directly to the required site.

Electroporation therapy (EPT) systems can also be employed for the administration of proteins and peptides. A device which delivers a pulsed electric field to cells increases the permeability of the cell membranes to the drug, resulting in a significant enhancement of intracellular drug delivery.

Proteins and peptides can be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of protein and peptide delivery is the ReGel injectable system that is thermo-sensitive. Below body temperature, ReGel is an injectable liquid while at body temperature it immediately forms a gel reservoir that slowly erodes and dissolves into known, safe, biodegradable polymers. The treatment agent is delivered over time as the biopolymers dissolve.

Protein and peptide pharmaceuticals can also be delivered orally. The process employs a natural process for oral uptake of vitamin $B_{12}$ in the body to co-deliver proteins and peptides. By riding the vitamin $B_{12}$ uptake system, the protein or peptide can move through the intestinal wall. Complexes are synthesised between vitamin $B_{12}$ analogues and the drug that retain both significant affinity for intrinsic factor (IF) in the vitamin $B_{12}$ portion of the complex and significant bioactivity of the drug portion of the complex.

Proteins and polypeptides can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al (1998), *Trends Cell Biol* 8, 84-87.

The treatment agents or formulations may also be administered transdermally, eg as a patch, gel, lotion, cream or oil.

It is preferred if the treatment agent (or agents) is administered orally.

It is further preferred if the treatment agent (or agents) is administered to the female reproductive system. For example, the treatment agent or agents may suitably be administered intravaginally using, for example, a gel or cream or vaginal ring or tampon. The treatment agent may also advantageously be administered by intrauterine delivery, for example using methods well known in the art such as an intrauterine device.

Typically, the gel or cream is one which is formulated for administration to the vagina. It may be oil based or water based. Typically, the treatment agent (or agents) is present in the cream or gel in a sufficient concentration so that an effective amount is administered in a single (or in repeated) application.

Typically, the vaginal ring comprises a polymer which formed into a "doughnut" shape which fits within the vagina. The treatment agent (or agents) is present within the polymer, typically as a core, which may dissipate through the polymer and into the vagina and/or cervix in a controlled fashion. Vaginal rings are known in the art. The vaginal ring may be disposable and is retained intravaginally during the woman's period and therefore contains sufficient of the treatment agent(s) to be released and to be effective during the woman's period. Alternatively, the vaginal ring may be used over a time interval of around three months to one year, during which time sufficient of the treatment agent(s) is released to have a beneficial effect over that period of time. It will be appreciated that the polymer from which the ring is made, the size and shape of the ring and the content of the treatment agent, as well as other parameters, may be selected by reference to whether the ring is for use in one cycle or for longer spells.

Typically, the tampon is impregnated with the treatment agent (or agents) and that a sufficient amount of the treatment agent (or agents) is present in the tampon.

Typically, the intrauterine device is for placing in the uterus over extended periods of time, such as between one and five years. Typically, the intrauterine device comprises a plastic frame, often in the shape of a "T" and contains sufficient of the treatment agent(s) to be released over the period of use. The agent is generally present within or encompassed by a slow-release polymer which forms part of the device, such as in the form of a "sausage" of agent which wraps around the long arm of the "T" which is typically covered with a controlled-release membrane. Intrauterine devices are known in the art.

Certain of the treatment agents are proteins or peptides which can be expressed from a nucleic acid molecule encoding them. Certain of the treatment agents are polynucleotides, and which may be expressed from a nucleic acid molecule encoding them. Methods, compositions and vectors for administering a nucleic acid molecule to a patient, such as a polynucleotide treatment agent of the invention, or a nucleic acid molecule encoding a treatment agent of the invention, are well known to a person of skill in the art.

Suitable delivery systems include liposomes, virosomes, microspheres or microcapsules, and genetic vectors such as viral and non-viral vectors.

The polynucleotide treatment agent, or a nucleic acid molecule encoding a treatment agent, may be administered systemically. Alternatively the inherent binding specificity characteristic of base pairing is enhanced by limiting the availability of the nucleic acid molecules of the invention to its intended locus in vivo, permitting lower dosages to be used and minimising systemic effects. Thus, the nucleic acid molecule may be applied locally to achieve the desired effect. The concentration of the polynucleotide treatment agent of the invention at the desired locus is much higher than if they were administered systemically, and the therapeutic effect can be achieved using a significantly lower total amount. The local high concentration of the polynucleotide treatment agent of the invention enhances penetration of the targeted cells.

The polynucleotide treatment agent, or a nucleic acid molecule encoding a treatment agent, can be delivered to the locus by any means appropriate for localised administration of a drug. For example, a solution of the nucleic acid molecules or vector can be injected directly to the site or can be delivered by infusion using an infusion pump. The nucleic acid molecules or vector also can be incorporated into an implantable device which when placed adjacent to the specific site, to permit them to be released into the surrounding locus.

The polynucleotide treatment agent, or a nucleic acid molecule encoding a treatment agent may be administered via a hydrogel material. The hydrogel is non-inflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10% to about 80% by weight ethylene oxide and from about 20% to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the oligonucleotides are admixed into the liquid to a concentration of about 1 mg polynucleotides per gram of hydrogel. The resulting mixture then is applied onto the surface to be treated, for example by spraying or painting during surgery or using a catheter or endoscopic procedures. As the polymer warms, it solidifies to form a gel, and the polynucleotides diffuse out of the gel into the surrounding cells over a period of time defined by the exact composition of the gel.

The polynucleotide treatment agent, or a nucleic acid molecule encoding a treatment agent can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylene vinyl acetate, polyvinyl acetate, ethylene vinyl alcohol, and derivatives thereof can be used to locally deliver the compounds of the invention. They can be incorporated into the material as it is polymerised or solidified, using melt or solvent evaporation techniques, or mechanically mixed with the material. In one embodiment, compounds of the invention are mixed into or applied onto coatings for implantable devices such as dextran coated silica beads, stents, or catheters.

The polynucleotide treatment agent, or a nucleic acid molecule encoding a treatment agent may be administered to a patient systemically for therapeutic and/or prophylactic purposes. The compounds may be administered by any effective method, for example, parenterally (eg intravenously, subcutaneously, intramuscularly) or by oral, nasal or other means which permit them to access and circulate in the patient's bloodstream. Nucleic acid molecules or vectors administered systemically preferably are given in addition to being locally administered, but also have utility in the absence of local administration. A dosage in the range of from about 0.1 to about 10 grams per administration to an adult human generally will be effective for this purpose.

The treatment agent may be expressed from any suitable polynucleotide, genetic construct or vector as is described herein, and delivered to the patient. Although a genetic construct for delivery of the treatment agent can be DNA or RNA, it is preferred if it is DNA.

Preferably, the genetic construct or vector is adapted for delivery to a human cell.

Means and methods of introducing a genetic construct into a cell in an animal body are known in the art. For example, the constructs of the invention may be introduced into cells by any convenient method, for example methods involving retroviruses, so that the construct is inserted into the genome of the cell (see, for example, Kuriyama et al (1991) *Cell Struc. and Func.* 16, 503-510). For the introduction of the retrovirus into cells, it is convenient to inject directly retroviral supernatant to which 10 µg/ml Polybrene has been added. For tissue exceeding 10 mm in diameter it is appropriate to inject between 0.1 ml and 1 ml of retroviral supernatant; preferably 0.5 ml. Alternatively, as described in Culver et al (1992) *Science* 256, 1550-1552, cells which produce retroviruses are injected.

Targeted retroviruses are also available for use in the invention; for example, sequences conferring specific binding affinities may be engineered into pre-existing viral env genes (see Miller & Vile (1995) *Faseb J.* 9, 190-199 for a review of this and other targeted vectors for gene therapy).

Other methods involve simple delivery of the construct into the cell for expression therein either for a limited time or, following integration into the genome, for a longer time. An example of the latter approach includes liposomes (Nässander et al (1992) *Cancer Res.* 52, 646-653).

For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288.

Other methods of delivery include adenoviruses carrying external DNA via an antibody-polylysine bridge (see Curiel *Prog. Med. Virol.* 40, 1-18) and transferrin-polycation conjugates as carriers (Wagner et al (1990) *Proc. Natl. Acad. Sci. USA* 87, 3410-3414).

The polynucleotide treatment agent, or a nucleic acid molecule encoding a treatment agent, may also be delivered by adenovirus wherein it is present within the adenovirus particle, for example, as described below.

In an alternative method, a high-efficiency nucleic acid delivery system that uses receptor-mediated endocytosis to carry DNA macromolecules into cells is employed, for example by conjugating the iron-transport protein transferrin to polycations that bind nucleic acids.

It will be appreciated that "naked DNA" and DNA complexed with cationic and neutral lipids may also be useful in introducing the compound of the invention into cells of the individual to be treated. Non-viral approaches to gene therapy are described in Ledley (1995) *Human Gene Therapy* 6, 1129-1144.

Alternative targeted delivery systems are also known such as the modified adenovirus system described in WO 94/10323 wherein, typically, the DNA is carried within the adenovirus, or adenovirus-like, particle. Other suitable viruses or virus-like particles include HSV, adeno-associated virus (AAV), vaccinia and parvovirus. Thus, it will be appreciated that a further aspect of the invention provides a virus or virus-like particle comprising a compound of the invention.

The invention also provides combinations (such as in a pharmaceutical formulation) of one or more of the treatment agents as described herein, and one or more agents presently used to treat menorrhagia, such as tranexamic acid or mefenamic acid.

The invention includes a kit of parts for combating menorrhagia comprising at least one agent that reduces the effect of PK1 on a PKR or at least one nucleic acid molecule that encodes a respective at least one agent that reduces the effect of PK1 on a PKR, and tranexamic acid or mefenamic acid.

The invention also includes a composition comprising at least one agent that reduces the effect of PK1 on a PKR, or at least one nucleic acid molecule that encodes a respective at least one agent that reduces the effect of PK1 on a PKR, and tranexamic acid or mefenamic acid.

The invention further includes a composition comprising at least one agent that reduces the effect of PK1 on a PKR, or at least one nucleic acid molecule that encodes a respective at least one agent that reduces the effect of PK1 on a PKR, and tranexamic acid or mefenamic acid for use in medicine.

The invention additionally includes a pharmaceutical composition comprising at least one agent that reduces the effect of PK1 on a PKR, or at least one nucleic acid molecule that encodes a respective at least one agent that reduces the effect of PK1 on a PKR, and tranexamic acid or mefenamic acid, and a pharmaceutically acceptable carrier, excipient or diluent.

The invention includes a method of combating menorrhagia in a female individual, the method comprising administering to the female at least one agent that reduces the effect of PK1 on a PKR or at least one nucleic acid molecule that encodes a respective at least one agent that reduces the effect of PK1 on a PKR (as described above), and tranexamic acid or mefenamic acid.

It is appreciated that the agent that reduces the effect of PK1 on a PKR and the tranexamic acid or mefenamic acid can be administered sequentially or (substantially) simultaneously. The may be administered within the same pharmaceutical formulation or medicament or they may be formulated and administered separately.

The invention includes the use of the combination of at least one agent that reduces the effect of PK1 on a PKR, or at least one nucleic acid molecule that encodes a respective at least one agent that reduces the effect of PK1 on a PKR, and tranexamic acid or mefenamic acid, in the preparation of a medicament for combating menorrhagia in a female individual.

The invention includes the use of at least one agent that reduces the effect of PK1 on a PKR, or at least one nucleic acid molecule that encodes a respective at least one agent that reduces the effect of PK1 on a PKR, in the preparation of a medicament for combating menorrhagia in a female individual, wherein the individual is administered tranexamic acid or mefenamic acid. Typically the female is administered the tranexamic acid or mefenamic acid at the same time as the medicament, although the female may have been (or will be) administered the tranexamic acid or mefenamic acid before (or after) receiving the medicament containing the at least one agent or the nucleic acid molecule.

The invention include the use of tranexamic acid or mefenamic acid in the preparation of a medicament for combating menorrhagia in a female individual, wherein the individual is administered at least one agent that reduces the effect of PK1 on a PKR, or at least one nucleic acid molecule that encodes a respective at least one agent that reduces the effect of PK1 on a PKR. Typically the female is administered the agent or the nucleic acid molecule at the same time as the medicament, although the female may have been (or will be) administered the agent or the nucleic acid molecule before (or after) receiving the medicament containing the tranexamic acid or mefenamic acid.

The invention also provides combinations (such as in a pharmaceutical formulation) of one or more of the treatment agents as described herein, and at least one agent which lowers estrogen levels or which antagonises the estrogen receptor. Such a combination may be useful in the treatment of endometriosis.

Agents which lower estrogen levels include gonadotropin releasing hormone (GnRH) agonists, GnRH antagonists and estrogen synthesis inhibitors. Agents which antagonise the estrogen receptor, ie estrogen receptor antagonists, include anti-estrogens.

Suitable GnRH agonists include leuprorelin (Prostap supplied by Wyeth) which may typically be administered at a level of 3.75 mg every 4 weeks subcutaneously (s.c.) or intramuscularly (i.m.) or 11.25 mg every 3 months s.c.; buserelin (Suprefact supplied by Shire) which is, typically administered at a level of 0.5 mg s.c. every 8 hours or 0.2 mg six times daily intranasally; goserelin (Zoladex supplied by Astra Zeneca) which is typically administered as a 3.6 mg s.c. implant every 28 days or 10.8 mg implant s.c. every 12 weeks; triptorelin (De-capeptyl sr supplied by Ipsen) which is typically administered at a level of 3 mg every 4 weeks; nafarelin (Synarel supplied by Searle); deslorelin (Somagard supplied by Shire); and histrelin/supprelin (Ortho Pharmaceutical Corp/Shire).

Suitable GnRH antagonists include teverelix (also known as antarelix); abarelix (Plenaxis supplied by Praecis Pharmaceuticals Inc); cetrorelix (Cetrotide supplied by ASTA Medica) which is typically administered at a level of 0.25-0.3 mg s.c. daily; and ganirelix (Orgalutran supplied by Organon) which is typically administered at a level of 0.25 mg daily s.c.

Suitable anti-estrogens include tamoxifen, Faslodex (ICI 182,780; Astra Zeneca), idoxifene (see Coombes et al (1995) *Cancer Res* 55, 1070-1074), raloxifene or EM-652 (Labrie, F et al, (2001) *J Steroid Biochem Mol Biol* 79, 213).

Suitable estrogen synthesis inhibitors include aromatase inhibitors. As is well known to those skilled in the art, examples of aromatase inhibitors include Formestane (4-OH androstenedione), Exemestane (steroidal, irriversible (type 1) inhibitors), Anastrozole (Arimidex) and Letroxole (non-steroidal, reversible (type 2) inhibitors). It may be useful to use inhibitors of both types in some patients (Harper-Wynne & Coombes (1999) *Eur J Cancer* 35, 744-746).

It may also be useful to include biphosphonates and/or calcium supplements in order to address the risk of osteoporosis, fracture or other musculoskeletal disorders.

The invention includes a kit of parts for combating endometriosis comprising at least one agent that reduces the effect of PK1 on a PKR or at least one nucleic acid molecule that encodes a respective at least one agent that reduces the effect of PK1 on a PKR, and at least one agent which lowers estrogen levels or which antagonises the estrogen receptor.

The invention also includes a composition comprising at least one agent that reduces the effect of PK1 on a PKR, or at least one nucleic acid molecule that encodes a respective at least one agent that reduces the effect of PK1 on a PKR, and at least one agent which lowers estrogen levels or which antagonises the estrogen receptor.

The invention further includes a composition comprising at least one agent that reduces the effect of PK1 on a PKR, or at least one nucleic acid molecule that encodes a respective at least one agent that reduces the effect of PK1 on a PKR, and at least one agent which lowers estrogen levels or which antagonises the estrogen receptor, for use in medicine.

The invention additionally includes a pharmaceutical composition comprising at least one agent that reduces the effect of PK1 on a PKR, or at least one nucleic acid molecule that encodes a respective at least one agent that reduces the effect of PK1 on a PKR, and at least one agent which lowers estrogen levels or which antagonises the estrogen receptor, and a pharmaceutically acceptable carrier, excipient or diluent.

The invention includes a method of combating endometriosis in a female individual, the method comprising administering to the female at least one agent that reduces the effect of PK1 on a PKR or at least one nucleic acid molecule that encodes a respective at least one agent that reduces the effect of PK1 on a PKR (as described above), and at least one agent which lowers estrogen levels or which antagonises the estrogen receptor.

It is appreciated that the agent that reduces the effect of PK1 on a PKR and the agent which lowers estrogen levels or which antagonises the estrogen receptor can be administered sequentially or (substantially) simultaneously. The may be administered within the same pharmaceutical formulation or medicament or they may be formulated and administered separately.

The invention includes the use of the combination of at least one agent that reduces the effect of PK1 on a PKR, or at least one nucleic acid molecule that encodes a respective at least one agent that reduces the effect of PK1 on a PKR, and at least one agent which lowers estrogen levels or which antagonises the estrogen receptor, in the preparation of a medicament for combating endometriosis in a female individual.

The invention includes the use of at least one agent that reduces the effect of PK1 on a PKR, or at least one nucleic acid molecule that encodes a respective at least one agent that reduces the effect of PK1 on a PKR, in the preparation of a medicament for combating endometriosis in a female individual, wherein the individual is administered at least one agent which lowers estrogen levels or which antagonises the estrogen receptor. Typically the female is administered the agent which lowers estrogen levels or which antagonises the estrogen receptor at the same time as the medicament, although the female may have been (or will be) administered the agent before (or after) receiving the medicament.

The invention include the use of at least one agent which lowers estrogen levels or which antagonises the estrogen receptor in the preparation of a medicament for combating endometriosis in a female individual, wherein the individual is administered at least one agent that reduces the effect of PK1 on a PKR, or at least one nucleic acid molecule that encodes a respective at least one agent that reduces the effect of PK1 on a PKR.

Typically the female is administered the agent or the nucleic acid molecule at the same time as the medicament, although the female may have been (or will be) administered the agent or the nucleic acid molecule before (or after) receiving the medicament.

All of the documents referred to herein are incorporated herein, in their entirety, by reference.

The listing or discussion of a prior-published document in this specification should not necessarily be taken as an acknowledgement that the document is part of the state of the art or is common general knowledge.

The invention will now be described in more detail with the aid of the following Examples.

EXAMPLE 1

Expression and Localisation of the Prokineticins [EG-VEGF and Bv8] and their Receptors in the Human Endometrium Across the Menstrual Cycle Summary The prokineticins (PK1 and PK2, also known as endocrine gland vascular endothelial growth factor (EG-VEGF) and Bv8 respectively), which bind to two closely homologous G-protein coupled receptors, PKR1 and PKR2, have been identified as novel angiogenic factors in endocrine tissue. However, little information was available on their expression and distribution in the uterus.

The objectives of the present study were to demonstrate expression of the prokineticins and their receptors in the normal human endometrium and to study the temporal variation in their expression across the menstrual cycle. In addition, regulation of PK1 by progesterone has been examined in normal endometrial tissue incubated in vitro.

We investigated the expression and localisation of prokineticins and their receptors in endometrial tissue across the menstrual cycle. Endometrial tissue (n=35) was obtained from women with regular menstrual cycles. Ethical approval from Lothian Research Ethics Committee and written informed consent were obtained. Temporal expression of PK1, PK2 and their receptors was assessed by real time (Taqman) quantitative RT-PCR. Localisation of PK1 was studied by immunohistochemistry, whilst distribution of PK2, PKR1 and PKR2 were examined by in situ hybridisation. In addition, we examined the effect of progesterone on the expression of PK1. Endometrial tissue (n=5) was incubated with 1 µM progesterone for 24 hours and RNA was extracted and subjected to quantitative RT-PCR.

PK1 expression was significantly increased in the secretory phase of the menstrual cycle compared with the proliferative phase (P<0.05), whilst expression of PK2 did not vary with the phase of the cycle. Both PKR1 and PKR2 showed significant upregulation in endometrial tissue during the transition from late secretory to the menstrual phase (P<0.05). PK1, PK2, PKR1 and PKR2 localised to glandular epithelial, stromal and endothelial cells of the endometrium and endothelial cells of the myometrium. Greater intensity of staining was observed for PKR1 compared with PKR2.

These data confirm cyclical regulation of prokineticins and their receptors in the human endometrium and suggest a role for these novel angiogenic factors in endometrial vascular function.

In this study the temporal expression of prokineticin 1 (PK1 or EG-VEGF) and prokineticin 2 (PK2 or Bv8) and their receptors (PKR1 and PKR2) have been examined in non-pregnant human endometrium. Expression of PK1 (by quantitative RT-PCR) was significantly increased in the secretory phase of the menstrual cycle compared with the proliferative phase (p<0.05). PK2 expression did not show significant variation with the phase of the menstrual cycle, whilst PKR1 and PKR2 expression were significantly elevated in the menstrual compared with the late secretory phase.

PK1 was localised by immunohistochemistry to glandular epithelial, stromal and vascular endothelial cells in the endometrium and endothelial and smooth muscle cells in the myometrium. Weak reactivity for PK2 was detected in similar locations to PK1. Expression of PKR1 varied in intensity between samples, but in some tissues strong reactivity was identified in glandular epithelial, stromal and endothelial cells, particularly in the functional layer, and in endothelial cells in the myometrium. In contrast, PKR2 was only weakly expressed. Treatment of endometrial tissue with 1 µM progesterone caused a 2.91 fold elevation in the expression of PK1 compared with controls (p<0.05). These data confirm the localisation and cyclical regulation of prokineticins and their receptors in human endometrium.

Materials and Methods

Patients and Tissue Collection

Endometrial biopsies at different stages of the menstrual cycle were obtained from women with regular menstrual cycles (25-35 days), who had not received a hormonal preparation in the three months preceding biopsy collection. Samples were collected either with an endometrial suction curette (Pipelle, Laboratoire CCD, Paris, France) or as full thickness endometrial biopsies (including the functional layer and basal-myometrial junction) from women undergoing hysterectomy for benign gynaecological indications. Shortly after collection, tissue was either snap frozen in dry ice and stored at −70° C. (for RNA extraction), fixed in neutral buffered formalin (NBF) and wax embedded (for immunohistochemical analyses), or placed in RPMI 1640 (containing 2 mmol l$^{-1}$ L-glutamine, 100 U penicillin and 100 µg ml$^{-1}$ streptomycin) and transported to the laboratory for in vitro culture.

Biopsies were dated according to stated last menstrual period (LMP) and confirmed by histological assessment according to criteria of Noyes and co-workers (Noyes et al (1975) *Am. J. Obstet. Gynecol.* 122: 262-263) Furthermore, circulating oestradiol and progesterone concentrations at the time of biopsy were consistent for both stated LMP and histological assignment of menstrual cycle stage. Samples were divided according to phase of menstrual cycle as menstrual (days 1-4), early to mid proliferative (EP-MP; days 5-10), late proliferative to ovulatory (LP-Ov; 11-14), early secretory (ES; 15-18) and mid to late secretory (MS-LS; 19-28). Ethical approval was obtained from Lothian Research Ethics Committee and written informed consent was obtained from all subjects before tissue collection.

Taqman Quantitative RT-PCR

RNA was extracted from endometrial biopsies obtained from across the menstrual cycle (n=35) using Tri Reagent (Sigma, Poole, UK) following the Manufacturer's instructions. RNA samples were quantified and were reverse transcribed using 5.5 mmol $l^{-1}$ $MgCl_2$, 0.5 mmol $l^{-1}$ of each deoxynucleotide triphosphate (dNTP), 2.5 µmol $l^{-1}$ random hexamers, ribonuclease inhibitor (0.4 U $µl^{-1}$) and 1.25 U $µl^{-1}$ Multiscribe reverse transcriptase (all from Applied Biosystems, Warrington, UK). RNA (400 ng) was added to each reverse transcription reaction and samples were incubated for 90 minutes at 25° C., 45 minutes at 48° C. and 5 minutes at 95° C. The reaction mix for the polymerase chain reaction (PCR) consisted of 1× mastermix, ribosomal 18S forward and reverse primers, Ribosomal 18S probe (50 nmol $l^{-1}$; all from Applied Biosystems, Warrington, UK), forward and reverse primers for PK1, PK2, PKR1 and PKR2 (300 nmol $l^{-1}$) and their probes (200 nmol $l^{-1}$) (all from Biosource UK, Nivelles, Belgium). The reaction mix (48 µl) was aliquoted into tubes and 2 µl cDNA was added. Duplicate 24 µl samples plus positive and negative controls were placed in a PCR plate and wells were sealed with optical caps. The PCR reactions were carried out using an ABI Prism 7700 (Applied Biosystems, Warrington, UK). All primers and probe were designed using the PRIMER express program (Applied Biosystems, Warrington, UK). The sequences of primers and probe are given in Table 1. Data were analysed and processed using Sequence Detector version 1.6.3 (Applied Biosystems, Warrington, UK) according to manufacturer's instructions. Results were expressed relative to an internal positive standard (cDNA obtained from a single sample of endometrial tissue) included in all reactions.

In Situ Hybridisation

Custom synthesised oligonucleotide double fluoroscein isothiocyanate (FITC)-labelled cDNA probes for PK2, PKR1 and PKR2 were obtained from Biognostik (Göttingen, Germany). Sections (5 µM) from full thickness human endometrial biopsies collected across the menstrual cycle (n=12) were cut onto gelatin-coated slides. Sections were dewaxed and rehydrated and then treated with proteinase K (20 µg $ml^{-1}$ in 100 mmol $l^{-1}$ Tris-HCl pH 7.6, containing 50 mmol $l^{-1}$ EDTA) for 15 minutes at 37° C. to enhance cDNA probe access. Sections were washed in diethylpyrocarbonate treated water and prehybridised for 4 hours at 30° C. with 25 µl of the hybridisation buffer supplied with the probe, which had been previously heated to 95° C. The sections were then hybridised overnight at 30° C. with the cDNA probe at 6 U $µl^{-1}$ for PKR1 and 12 U $µl^{-1}$ for PK2 and PKR2 in hybridisation buffer. Following hybridisation, sections were washed for 2×5 minutes in 1× standard saline citrate (SSC) at room temperature and 2×15 minutes in 0.1×SSC at 39° C. After rinsing in TBS, endogenous peroxidase activity was quenched with 10% (v/v) $H_2O_2$ in methanol at room temperature. The FITC-labelled probes were detected using standard immunohistochemical reagents with an additional amplification step (TSA Biotin System, NEN Life Science Products, Hounslow, UK). Sections were incubated with blocking buffer for 30 minutes. Conjugated anti-FITC-horseradish peroxidase (Roche, Diagnostics Ltd., Lewes, UK) was added at a dilution of 1 in 200 in blocking buffer and the sections incubated for 30 minutes. After washing, biotinyl tyramide amplification reagent (1 in 50) was applied to each slide and incubated for 15 minutes. Streptavidin-horseradish peroxidase (1 in 100) was applied after washing and incubated for 30 minutes and probe localisation visualised with 3,3'-diaminobenzidine (DAB) substrate. Control sections were treated with a double FITC-labelled oligonucleotide probe containing the same proportion of cytosine (C) and guanine (G) bases as the PK2, PKR1 and PKR2 probes to assess background hybridisation. All treatments were carried out at room temperature unless otherwise specified.

Immunohistochemistry

Endometrial sections (5 µm) from across the menstrual cycle (n=12) were dewaxed in xylene and rehydrated using decreasing grades of ethanol. Antigen retrieval was performed by treating sections for 5 minutes in a pressure cooker in boiling 0.1% citrate buffer, pH 3.0. Endogenous peroxidase activity was quenched with 10% (v/v) $H_2O_2$ in methanol at room temperature. Non-immune swine serum (20% serum in TBS) was applied for 1 hour before overnight incubation at 4° C. with rabbit anti-human prokineticin 1 (*Phoenix* Pharmaceuticals Inc., Belmont, Calif.) at a dilution of 1 in 2000. An avidin-biotin peroxidase detection system was then applied (DAKO Ltd., Cambridge, UK) with DAB as the chromagen.

Tissue Incubation

Endometrial biopsies (n=5) were minced finely with scissors and divided into two portions. The tissue was incubated overnight at 37° C. in a humidified 5% $CO_2$ incubator in 2 ml Phenol Red Free D-MEM/F-12 medium with L-glutamine (Invitrogen Ltd., Paisley, UK) containing 100 IU penicillin and 100 µg streptomycin. The tissue was then treated for 24 hours in the same medium either in the presence of 1 µM progesterone or an equivalent volume of ethanol.

Statistics

Where appropriate, data were subjected to statistical analysis with ANOVA and Fishers PLSD tests (Statview 4.0; Abacus Concepts Inc., Piscataway, N.J., USA) and statistical significance accepted when p<0.05.

Results

Figure 1:
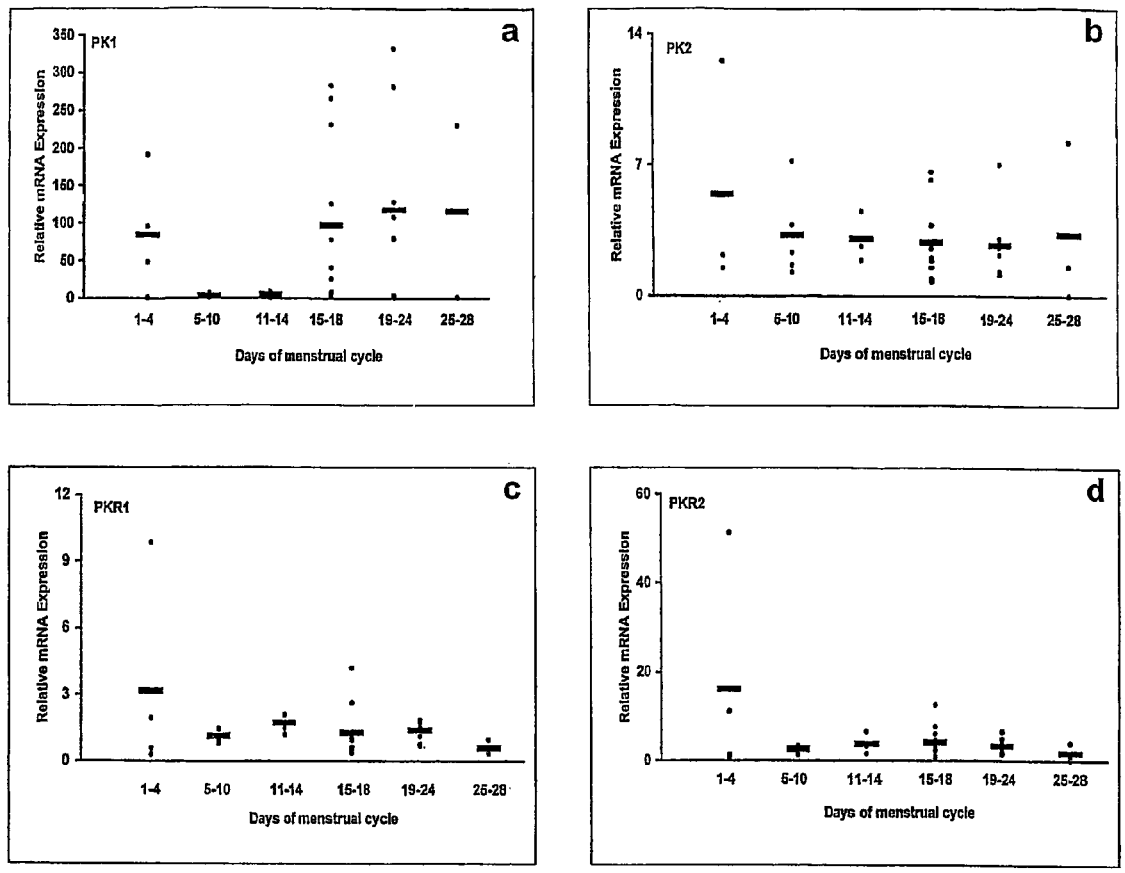
FIG. 1: Quantitative RT-PCR of PK1 (a), PK2 (b), PKR1 (c) and PKR2 (d) in the human endometrium across the menstrual cycle. Each symbol represents one tissue sample. Means indicated by solid bar.

The expression of PK1 and PK2 and their receptors across the menstrual cycle was examined by real time quantitative RT-PCR FIG. 1a). PK1 was detected in all tissue samples examined (N=35) and was significantly elevated in the secretory phase of the menstrual cycle (days 15-28) compared with the proliferative phase (days 5-14) (107.35±24.07 vs 3.29±0.98; p<0.01). Expression of PK1 in the menstrual phase of the cycle (84.43±40.52) did not differ significantly from the proliferative or secretory stages. PK2 expression was also present in all samples examined (FIG. 1b), but did not show significant variation with phase of the menstrual cycle (Menstrual: 5.44±2.53; Proliferative: 3.17±0.61; Secretory 2.88±0.47). PKR1 and PKR2 expression did not differ on comparison of proliferative and secretory phases of the menstrual cycle (1.38±0.16 vs 1.21±0.19 and 3.08±0.52 vs 3.45±0.62 respectively), but significantly higher expression of both PKR1 and PKR2 were detected in the menstrual phase of the cycle (3.17±2.26; 16.16±12) compared with the secretory phase (p<0.05 for PKR1; p<0.01 for PKR2) (FIGS. 1c and 1d)). The difference between menstrual phase and proliferative phase was also significant for PKR2 (p<0.01).

Figure 2:
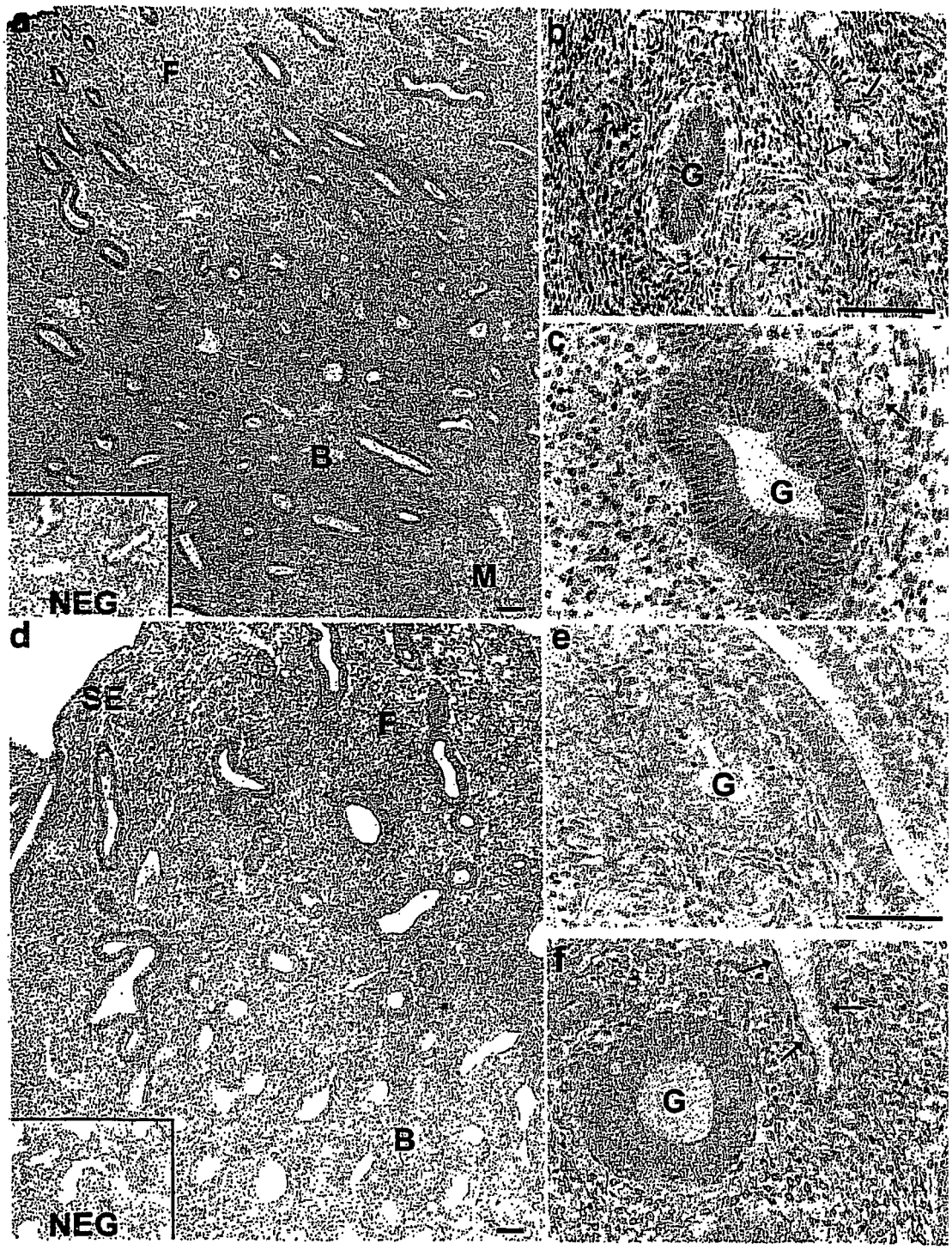
FIGS. 2a-2c: Immunohistochemical localisation of PK1 in human endometrial tissue (functional layer and basal-myometrial junction). Glandular epithelial staining (G) was present in both basal (B) and functional (F) layers and in smooth muscle reactivity was detected in the myometrium (M). Stromal cell expression was detected in the functional (FIG. 2b) and basal (FIG. 2c) layers and endothelial cell reactivity was present throughout the tissue (see arrows in FIGS. 2b and 2c). NEG=Negative control; Scale bars=100 µM (FIG. 2a) and 50 µM (FIG. 2b).
FIGS. 2d-2f: In situ hybridisation of PK2 in human endometrial tissue (functional layer and basal-myometrial junction). PK2 was expressed in glandular epithelial cells (G)

Immunohistochemical staining for PK1 was performed in full thickness human endometrial biopsies collected from across the menstrual cycle (FIG. 2a-2c). Reactivity was variable and some tissues were negative. Expression was detected in cytoplasmic and perinuclear locations in the glandular epithelium in functional and basal layers (FIGS. 2b and 2c). Perinuclear immunoreactivity was observed in endothelial and stromal cells in the functional layer, with weaker endothelial and stromal staining in the basal layer. Endothelial cells lining blood vessels in the myometrium and myometrial smooth muscle cells also displayed perinuclear immunoreactivity.

PK2 expression was studied by in situ hybridisation (FIG. 2d-2f). In general, expression was weak and was not present in all samples examined. Reactivity was detected in the cytoplasm of glandular epithelial cells predominantly in the functional layer (FIG. 2f) with stronger staining towards the luminal surface of the epithelium. The functional layer also weakly expressed reactivity in stromal and endothelial cells (FIG. 2f) and some vascular staining was also present in the basal layer. PK2 was also expressed in the vasculature in the myometrium with infrequent weak staining of myometrial smooth muscle cells.

The endometrium showed strong expression of PKR1 by in situ hybridisation, although samples obtained during the late proliferative to mid-secretory phases of the menstrual cycle showed very weak or negative staining for PKR1. Reactivity was detected in the cytoplasm of glandular epithelial cells in the functional and basal layers, together with endothelial cells in both layers (FIGS. 3a-3c). Stromal cells also displayed reactivity, but it was stronger in the functional layer (FIG. 3c). There was prominent expression of PKR1 in the blood vessels in the myometrium and the smooth muscle cells also displayed reactivity. PKR2 was less frequently expressed than PKR1 (FIGS. 3d-3f) and staining was weak and confined to the cytoplasm of glandular epithelial cells and endothelial cells predominantly in the functional layer (FIG. 3f).

The significant upregulation of PK1 expression in the secretory phase of the menstrual cycle suggested possible regulation of PK1 by progesterone. Therefore to investigate this possibility, samples of endometrial tissue (n=5) were incubated for 24 hours in the presence of 1 µM progesterone or an equivalent volume of ethanol. Tissue incubated with progesterone showed a 2.91(±0.75) fold increase in PK1 expression, by Taqman RT-PCR, compared with the controls.

TABLE 1

| Primer | Sequence [5' → 3'] |
|---|---|
| PK1 Forward | GTGCCACCCCGGCAG |
| PK1 Reverse | AGCAAGGACAGGTGTGGTGC |
| PK1 Probe | FAM-ACAAGGTCCCCTTCTTCAGGAAACGCA-TAMRA |
| PK2 Forward | TTGGGCGGAGGATGCA |
| PK2 Reverse | AAATGAAGTCCGTAAACAGGCC |
| PK2 Probe | FAM-CACTTGCCCATGTCTGCCAGGCT-TAMRA |
| PKR1 Forward | TCTTACAATGGCGGTAAGTCCA |
| PKR1 Reverse | CTCTTCGTGGCAGGCAT |
| PKR1 Probe | FAM-TGCAGACCTGGACCTCAAGACAATTGG-TAMRA |
| PKR2 Forward | GCTCTGTGCCTCCGTCAACT |
| PKR2 Reverse | CCAGCAAGGCATTGGTGG |
| PKR2 Probe | FAM-CCTGCGCACCGTCTCCCTCTACG-TAMRA |

EXAMPLE 2

Treatment of Menorrhagia with a PK1 Antagonist

A patient suffering from menorrhagia is administered an anti-PK1 antibody such as monoclonal antibody 4H9 described in published US Patent Application No. 2002/0192634 A1 at a dosing quantity and frequency such that the therapeutic level of active agent at the site of treatment is maintained at a level ideally $EC_{90}$ but preferably not less than $EC_{50}$ throughout the treatment period. Typically, the antibody is maintained at a concentration of at least 10 µg/ml. The treatment is delivered orally or more locally depending on patient acceptability, avoidance of side effects and systemic bioavailability.

EXAMPLE 3

Treatment of Dysmenorrhoea with a PK1 Antagonist

A patient suffering from dysmenorrhoea is administered an anti-PK1 antibody such as monoclonal antibody 4H9 described in published US Patent Application No. 2002/0192634 A1 at a dosing quantity and frequency such that the therapeutic level of active agent at the site of treatment is maintained at a level ideally $EC_{90}$ but preferably not less than $EC_{50}$ throughout the treatment period. Typically, the antibody is maintained at a concentration of at least 10 µg/ml. The treatment is delivered orally or more locally depending on patient acceptability, avoidance of side effects and systemic bioavailability.

EXAMPLE 4

Treatment of Endometriosis with a PK1 Antagonist

A patient suffering from endometriosis is administered an anti-PK1 antibody such as monoclonal antibody 4H9 described in published US Patent Application No. 2002/0192634 A1 at a dosing quantity and frequency such that the therapeutic level of active agent at the site of treatment is maintained at a level ideally $EC_{90}$ but preferably not less than $EC_{50}$ throughout the treatment period. Typically, the antibody is maintained at a concentration of at least 10 µg/ml. The treatment is delivered orally or more locally depending on patient acceptability, avoidance of side effects and systemic bioavailability.

The invention claimed is:

1. A method of treating endometriosis in a female individual, the method comprising administering to the individual at least one agent that reduces the effect of prokineticin 1 (PK1) on a prokineticin receptor (PKR), wherein the agent that reduces the effect of PK1 on a PKR is an anti-PK1 antibody.

2. A method of treating endometriosis according to claim 1 further comprising administering to the individual at least one agent which lowers estrogen levels or which antagonises the estrogen receptor.

3. A method according to claim 2 wherein the at least one agent which lowers estrogen levels or which antagonises the estrogen receptor is a gonadotropin releasing hormone (GnRH) antagonist.

4. A method according to claim 3 wherein the GnRH antagonist is teverelix, abarelix, cetrorelix or ganirelix.

5. A method according to claim 1 wherein the anti-PK1 antibody is selected from 1C6, 2A3, 2A8 and 4H9.

* * * * *

UNITED STATES PATENT AND TRADEMARK OFFICE
CERTIFICATE OF CORRECTION

PATENT NO.      : 7,615,210 B2                                              Page 1 of 1
APPLICATION NO. : 10/569920
DATED           : November 10, 2009
INVENTOR(S)     : Jabbour et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 24 days.

Signed and Sealed this

Fourteenth Day of December, 2010

David J. Kappos
*Director of the United States Patent and Trademark Office*